United States Patent [19]

Klausz

[11] Patent Number: 4,677,681
[45] Date of Patent: Jun. 30, 1987

[54] METHOD FOR ELIMINATING THE DIFFUSED RADIATION IN A RADIOLOGY IMAGE

[75] Inventor: Rémy Klausz, Paris, France

[73] Assignee: Thomson-CSF, Paris, France

[21] Appl. No.: 488,636

[22] Filed: Apr. 26, 1983

[30] Foreign Application Priority Data

May 4, 1982 [FR] France .............................. 82 07751

[51] Int. Cl.[4] ........................................... G01N 21/00
[52] U.S. Cl. .................................. 382/6; 250/363 S; 378/2; 378/7; 378/70; 382/54
[58] Field of Search ........................................ 378/1–2, 378/21, 5, 7, 70, 145–146, 149, 158–161, 210; 250/363, 363 SD, 366, 369; 350/162.16, 168, 266; 364/414; 358/111; 382/6, 42, 54, 65

[56] References Cited

U.S. PATENT DOCUMENTS

| | | | |
|---|---|---|---|
| 3,860,821 | 1/1975 | Barrett | 250/363 |
| 3,950,613 | 4/1976 | Macovski | 378/145 |
| 4,123,654 | 10/1978 | Reiss et al. | 378/5 |
| 4,209,780 | 6/1980 | Fenimore et al. | 382/42 |
| 4,315,146 | 2/1982 | Rudin | 378/146 |
| 4,433,427 | 2/1984 | Barnea | 378/149 |
| 4,493,096 | 1/1985 | Rieke | 378/7 |
| 4,497,062 | 1/1985 | Mistretta et al. | 378/158 |

*Primary Examiner*—Leo H. Boudreau
*Attorney, Agent, or Firm*—Roland Plottel

[57] ABSTRACT

A method is disclosed for eliminating the diffused radiation in a radiology image. The method fundamentally consists in interposing a mask comprising a finite number of areas absorbent to X-rays between the X-ray source and the object which is to be examined, in detecting the corresponding fundamental image in order to deduce from the areas of the same which correspond to the parts eliminated from the beam a distribution of the diffused radiation throughout the image, and in correcting the fundamental image based on this distribution. The method is particularly applicable to medical radiology.

18 Claims, 3 Drawing Figures

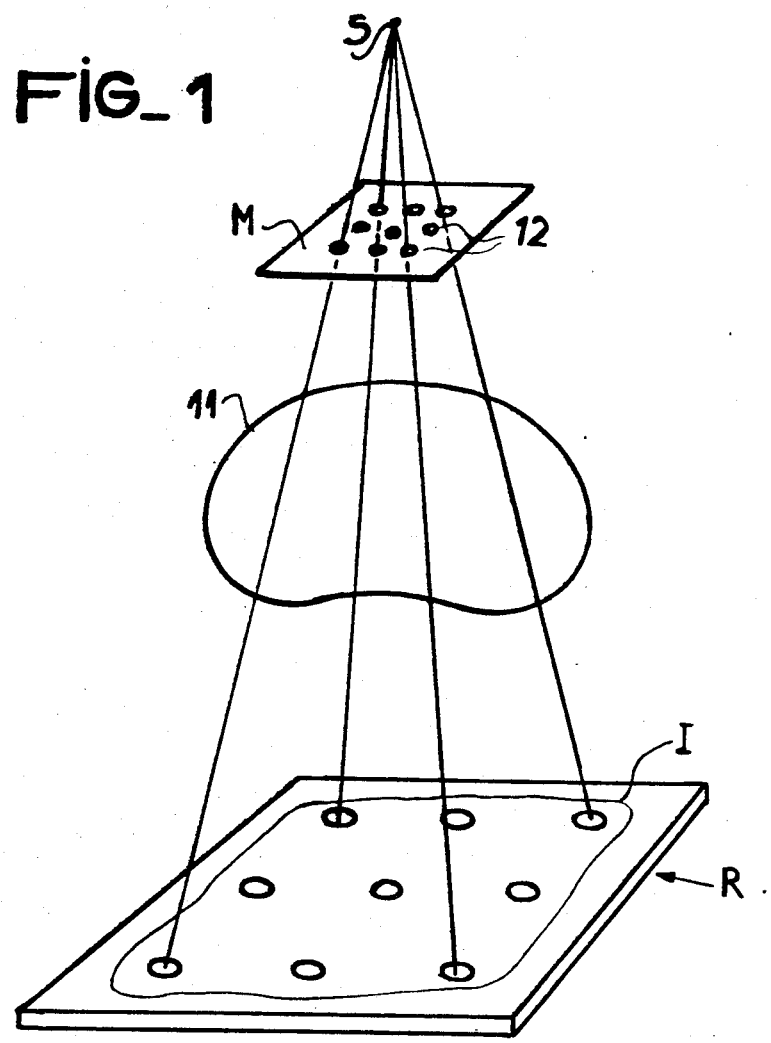
FIG_1
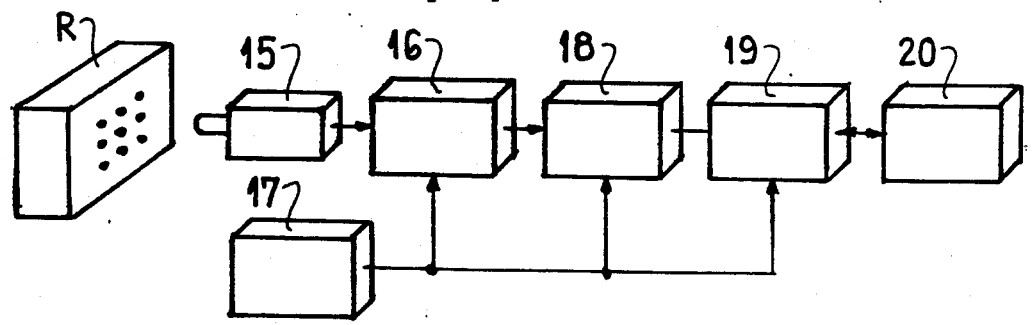
FIG_2

FIG_3
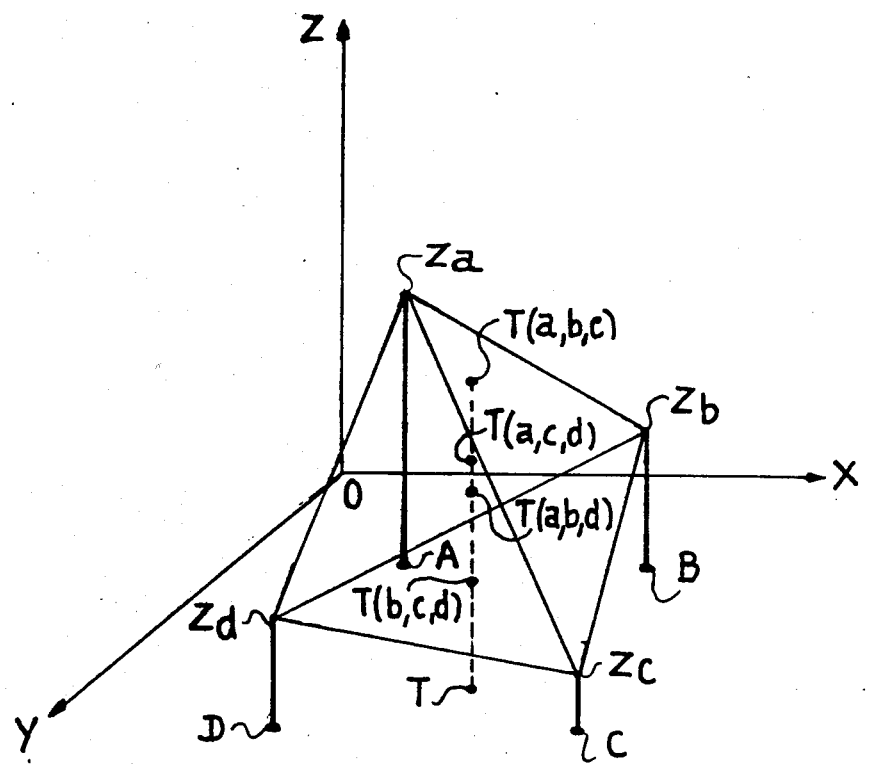

METHOD FOR ELIMINATING THE DIFFUSED RADIATION IN A RADIOLOGY IMAGE

The invention relates to a method for processing a radiological image for the purpose of detecting the contribution of diffuse X-ray radiation and of correcting the image by removing the resultant interference component.

BACKGROUND OF THE INVENTION

A conventional radiology installation principally comprises an X-ray source emitting a wide beam in the direction of a receiver, which may be a film or a brightness intensifier, situated at a definite distance from the source. The structure which is to be examined is positioned between the source and this receiver.

The image obtained is representative of the absorption of the radiation in the structure examined, but the contrasts are restricted by an interference effect, namely X-ray diffusion. This does not constitute a significant absorption, but in a deflection of particular rays, which may occur within the structure which is to be examined as well as within a brightness intensifier, if the installation comprises one. The X-rays are normally propagated in a straight line except in the case of interaction of diffusion at a given point of the path; this point then acts as a secondary transmission source. In other words, the diffusion effect has the result that particular points of the photoluminescent detector receive complementary photons which are deficient from other points, thus impairing the clearness of the image.

To act against this effect, an anti-diffuser grid may be placed between the structure which is to be examined and the brigtness intensifier, this grid having the effect of absorbing a part of the radiation diffused in the said structure.

A more effective method is that referred to as "traveling apertures". The radiological installation is complemented by interposing two diaphragms comprising apertures in the form of a slot, the said slots being arranged and constantly maintained in mutual homothetic relationship. One of the diaphragms is placed between the source and the structure to be examined, whereas the other is placed between the said structure and the receiver. A relative displacement is created between the slots and the structure to be examined. The image is thus acquired "line by line", each line being unaffected by a diffusion component. A modern tomodensitometer may be utilised in a manner simulating the method of traveling apertures, since the X-ray beam is flat and emitted in the direction of a row of detectors. It is then sufficient to move the structure to be examined with respect the the source-detectors array without causing this array to turn as would normally be the case for acquiring an image by tomodensitometry.

As opposed to these methods which consist in an elimination of the diffusion interference component, another approach is known which consists in trying to pre-establish the diffusive function through all the image points and in correcting this image accordingly. An article disclosing this method was published in issue No. 142 of the "RADIOLOGY" review of January 1982. This method may be effective in eliminating the diffusion component established in the brightness intensifier, but it would be difficult to hope to correct in this manner the diffusion interference component formed in the structure to be examined itself, since the first component is of optical nature linked with the image, whereas the second is a physical diffusion of X-rays as a function of the whole volume which is to be examined. However, this second component is very substantial quantitatively, and may in particular cases be of the same order of magnitude as the component representing the image.

The invention has as an object a method able to establish the pattern of the total or overall diffusion component at all points of the image, that is to say, a pattern obtained from data drawn from the image obtained itself and consequently taking into account the diffusion component originating within the structure to be examined.

SUMMARY OF THE INVENTION

To this end, the invention consequently primarily relates to a method for processing a radiological image of a structure, which image is obtained from an irradiation of the said structure by means of a beam of penetrating radiation emitted by a source, for example by an X-ray source, and comprises a significant component and an overall diffusion interference component, characerised in that it consists in:

(a) eliminating a finite number of parts of the said beam along different directions, between the source and the said structure, (b) detecting at least one fundamental radiological image under such conditions, (c) deducing from the areas of the said fundamental image corresponding to the parts eliminated from the said beam, a distribution of the diffused radiation, substantially throughout the image, and (d) correcting the said fundamental image or possibly an analogous image, by means of the said distribution of the diffused radiation.

The term "analogous image" denotes for example, a complete image obtained by means of a complete beam, or an image derived from at least one fundamental image, in which the missing parts have been replaced.

The said parts may be eliminated from the said beam in a simple manner by interposing a mask carrying a finite number of areas which are substantially completely absorbent as regards the said radiation, between the source and the structure to be examined. On the other hand, the distribution of the diffused radiation throughout the image may be determined by selecting the areas of the fundamental image corresponding to the eliminated parts of the beam, whilst making allowance for the intensities of diffused radiation in these areas and applying an interpolation method, known per se, such that knowing the measured values of the intensity of the diffused radiation, it is possible to deduce other diffused radiation intensity values corresponding to other areas of the image.

According to another aspect of the invention, the correction of the said fundamental image or of the said analogous image, will be obtained by substracting therefrom an image representing the said distribution of the diffused radiation.

According to another important feature of the invention, the method described above is complemented in order to obtain a complete corrected image. To this end, it is possible in particular to generate an aforesaid analogous image of the said fundamental image by completing this latter with at least some parts of another image of the said structure reproducing at least the said areas corresponding to the said parts eliminated from the beam, this other image being preferably established within a short time of the first.

BRIEF DESCRIPTION OF THE DRAWINGS

The invention will now be further described, by way of example, with reference to the accompanying drawings, in which:

FIG. 1 diagrammatically illustrates one embodiment of a radiological installation incorporating the means required for carrying out the method of the invention, FIG. 2 illustrates an installation for taking images and for digital processing of the images obtained, and FIG. 3 illustrates one of the methods of interpolation usable within the scope of the method.

DESCRIPTION OF THE PREFERRED EMBODIMENTS

The fundamental concept of the invention can be easily grasped by examining the diagram of FIG. 1. This Figure shows a radiological installation which comprises a source S of penetrating radiation (typically being an X-ray source) and a receiver R denoted in this case by its plane for visual display of the radiological image. In practice, this receiver may be a brightness intensifier which is well known and not free (as stated earlier) of inherent optical faults generating a supplementary diffusion component. The structure 11 which is to be examined is positioned between the source S and the receiver R.

If a finite number of parts of the beam emitted by the source S are eliminated, along different directions, between the said source and the structure 11, the resulting radiological image I should in theory be dotted with as many dark areas which have not received any radiation. If on the contrary a certain image is observed, this can be only that of the overall diffusion component in these areas of the fundamental image I. Everywhere else, the image is practically identical to that which would have been obtained with a complete beam, since all that is absent is the contribution of the radiation which would have been diffused from the eliminated parts of the beam, which contribution may be ignored if these represent a small part only of the overall radiation of the source S. In practice, a finite number of parts of the beam are eliminated by interposing a mask M carrying a particular number of areas 12 considered as being totally absorbent as regards X-ray radiation, between the source S and the structure 11, as illustrated in FIG. 1. These wholly absorbent areas will be formed by means of deposits of sufficient thickness of a material of high density, such as lead or tantalum. Their thickness is determined so as to produce a very substantial attenuation within the energy band currently utilised in radiology (for example up to 150 keV) and in particular a sufficient attenuation such that the weak residual radiation transmitted through these deposits is lower than the sensitivity threshold of the receiver. In particular, if, as will be shown in the following, the subsequent utilisation of the radiological images requires a "digitalisation" of these images into words of n bits, it is sufficient for the attenuation to exceed the value denoted by the least representative bit. An attenuation equal to $k2^n$ will consequently be adopted, k being a safety factor equal to at least 3 or 4. By way of example, if the digitalisation is performed into words of 8 bits, $$2^n = 2^8 = 256$$

An attenuation comprised between $10^3$ and $10^4$ will be adequate.

For a simple application of the subsequent digital processing of the image, a baffle or mask will be selected of which the said opaque areas form a regular geometrical pattern, for example, with a periodicity along at least one direction of the plane of the mask. In the example of FIG. 1, this simply consists of a square-mesh checkering by opaque dots. The radiological image thus obtained is referred to as the "fundamental image" since it is on the basis of the same that several operations will be performed, leading on the one hand to correction of this image or of an analogous image for the purpose of eliminating the diffusion component, and on the other hand to complete it with the parts which had necessarily been removed from the same at the instant of its acquisition by the presence of the mask.

The following stages of the method of the invention have the purpose of deducing from the areas of the fundamental image corresponding to the occulted parts of the beam, a distribution of the diffused radiation throughout the image. At this stage of the method, it is advantageous to resort to digital imagery techniques consisting in performing the required processing operations on "digitalised" images, that is to say, converted into digital data representative of the brightness of a particular number of dots of the image. One type of installation for digitalisation of radiological images is shown diagrammatically by way of a reminder in FIG. 2. The image I displayed on the screen of the receiver R (brightness intensifier) is analysed line by line by means of a television camera 15 whose video signal output is connected to the input of a sampling circuit 16 which converts the signal into succession of steps at the frequency of a clock 17. The sampled signal is applied to the input of an analog-digital converter 18. Each value of the video signal sampled is then converted into a word of n bits (n depending on the accuracy required) and these words are stored in a memory 19. The memory may be reread later and the values stored may be modified by any appropriate processing by means of a computer 20 coupled to the memory 19. A final visual display will be performed by "reading" the image thus processed and by reconstituting the video signal by means of a digital-analog converter (not illustrated) and by feeding the same to the video input of a television apparatus.

The fundamental image described in the foregoing is consequently "digitalised" in this manner.

On the other hand, a reference image is obtained in the same conditions but in the absence of the structure 11 which is to be analysed. This image is also "digitalised" and stored in the following manner: the value 1 is allotted to all the points at which the intensity of the radiation received is lower than a particular threshold (these are the points corresponding to the absorption areas) and the value 0 is allotted to all the other points. An image of the "all or nothing" kind is obtained in this manner, intended to serve the purpose of performing a first series of operations on the fundamental image. The reference image may be acquired once and for all. It should be observed at this stage of the description that the different operations which will be described (subtractions, averaging point by point, additions . . . ) do not in any way mean that the intermediate images are put on visual display; on the contrary, "image" is understood to refer to the totality of the digital data initially representing a fundamental image or a reference image and having undergone the same conversions.

The reference image is to serve the purpose of permitting precise extraction of the areas of the fundamental image corresponding to the projections of the opaque areas of the mask. As a matter of fact, if a logic AND aperation is performed between the two homologous elementary parts (in other terms point by point) of the two images stored, the result is given by the following truth table:

| Mask | Fundamental Image | |
|---|---|---|
| 0 | $\phi$ | 0 |
| 1 | $\phi$ | $\phi$ |

In other words, the result of the operation is zero if the corresponding point of the mask is transparent, and is equal to the fundamental image if the corresponding point of the mask is opaque to X-rays. However, the areas of the fundamental image which are retained by this operation, are in no way representative of an image of the structure 11. On the contrary, they are the manifestation of the overall diffusion component (occurring between the source and the display screen of the receiver R) at different areas of the image. There has in effect been carried out at this stage of the method described, an adequate sampling operation (within the meaning of the Shannon theory) for reconstituting the diffusion component at the same time as generating a large part of the image of the structure 11. This reconstitution may be performed by application, for example by digital processing programmed in the computer 20, of any known interpolation method, the diffusion component at each point being estimated on the basis of knowing the same for the closest sampling points. A possible method of interpolation will now be described with reference to FIG. 3 which illustrates the diffusion component witin a three-dimensional orthonormal system of coordinates OXYZ. The plane XOY represents the visual display plane for the intermediate image resulting from the AND operation referred to in the foregoing between the fundamental image and the reference image, it being understood that this intermediate image exists in digital form only and its reconstitution in visible form is not of interest. The point T is that at which it is sought to determine a value of the diffusion component, recognising the values at the closest points A,B,C and D. These values are represented by the heights $Z_a, Z_b, Z_c$ and $Z_d$ plotted starting from the points A,B,C and D of the plane OXY. The interpolation method consists in determining the equations for the four planes passing through the triplets $Z_a, Z_b, Z_c$ - $Z_a, Z_b, Z_d$ - $Z_a, Z_c, Z_d$ and $Z_b, Z_c, Z_d$, and then the coordinates of the points of intersection between each of these planes and the line perpendicular to the plane OXY passing through the point T. Let T(abc), T(abd), T(acd) and T(bcd) be these points, and the value of the diffusion component at the point T is determined by establishing the mean of the projections of these four points along the axis OZ.

All the operations referred to in the foregoing are simple (determining a plane, whilst knowing three of its points) and may easily be programmed in the computer 20. The storage capacity needed is low, inasmuch as the value of the diffusion component at any point situated within the quadrangle ABCD is deduced from the equations of the same four planes, the parameters of these planes easily being able to be stored once and for all. The known interpolation method referred to above is obviously not the only one applicable within the scope of the invention. In particular, accuracy may be improved by taking into account knowledge of the diffusion determined at other and more distant points and by causing surfaces corresponding to equations of higher order to pass through all these points.

When this interpolation method has been completed for all the sampling points of the intermediate image, a complete image is obtained (in digital form) of the distribution of the diffused radiation within the radiological image. The method of the invention could then be accomplished in simple manner by subtracting this diffusion image from the fundamental image, but it could be difficult to utilise the radiological image obtained in this manner because of the portions of the image of the structure 11 which could not be obtained because of interposing the mask M. This will most frequently lead to completing the corrected image or on the contrary to application of the correction throughout an already completed fundamental image (subtraction of the diffusion distribution image).

It should be observed that the spreading function of the system imposes a minimum surface on each elementary absorbent area of the mask, so that the "shadow carried" may be detected in the fundamental image. If the mask is actually dotted with elementary areas having a minimum surface, the radiological image will be curtailed very little and it will be sufficient to complete the missing parts by means of an interpolation performed on the basis of points close to the said parts, within the image itself. Another possibility applicable in all cases consists in adding at least the corresponding parts of the missing parts drawn from another image, preferably taken within a short time of the first, of which the acquisition and digitalisation will be peformed after having removed or displaced the mask or else after having replaced the same by a different mask. Several possible solutions are described in the following.

According to a first modification, a complementary image of the fundamental image may be generated from a beam comprising only the parts eliminated for producing this fundamental image, a digital conversion may be performed on this complementary image and this may be added point for point to the corrected fundamental image. In concrete manner, the complementary image will be obtained by taking another exposure of the structure 11 after replacing the mask M with a complementary mask (not illustrated), that is to say a mask which is wholly absorbent except at areas homologous to the absorbent areas of the mask M. The acquisition of the complementary image will be peformed within as short a time as possible of the acquisition of the fundamental image. It should be observed that in this very partial image of the structure 11, the diffusion component is very small and may be disregarded. It will consequently be sufficient to "add" the complementary image digitally to the corrected fundamental image without exposing it to the corrective process. The complementary mask should obviously be positioned precisely as and instead of the mask M so that the fundamental image may be actually completed with its missing parts. The two exposures may be taken at specified dosage if the structure to be analysed is a living being.

Another solution may purely and simply consist in exposing another radiological image without a mask, equally within a short a time as possible of the fundamental image and in performing the correction on this complete image, the fundamental image in this case serving only the purpose of determining the distribution of the diffusion component. If the structure to be analysed is a living entity, the complete analogous exposure may be taken at rated dosage whereas the fundamental image may be exposed with a lower X-ray dosage sufficient for determination of the distribution of the diffusion component, possibly subject to application of a correction factor.

A third solution consists in producing two fundamental images from two beams lacking any common eliminated parts. In concrete terms, this may be performed simply by displacing the mask M within its own plane, between two exposures. The "analogous image" within the meaning defined in the foregoing may then be obtained by establishing the average of the homologous parts of the two fundamental images which do not correspond to the parts eliminated from the one beam or the other, and by "completing" this intermediate image by adding to the same (point by point) the parts of each fundamental image which correspond to the parts eliminated from the beam for generating the other fundamental image. The correction is then applied to the "analogous image" obtained in this manner. The correction may also be applied separately to each fundamental image before combining them. The interest of this last procedure resides in that it offers the possibility of double determination of the "image" of the diffusion component from two different positions of the mask and consequently the opportunity to verify the precision of the interpolation algorithm selected. Each fundamental image may be taken at a lower dosage if the structure to be analysed is a living being.

Furthermore, the setting of the mask in the one position or the other may be determined easily, for example, by acquiring two reference images (images of the mask in the absence of the structure 11) corresponding to these two possible positions of the mask. For exposures at a fast rate of recurrence (for example angiography), it will also be possible to mount the mask on a movable carrier to impart to it an alternating linear displacement or a rotary motion, within its own plane, and to synchronise the exposures with this motion. This procedure will be employed for example, to acquire a plurality of fundamental images which will thereafter be combined in pairs to end with the visual display of a succession of corrected images.

The invention is obviously not limited to the method described. Other modifications are also possible, especially in the configuration of the mask. A recurrent "polkadot" structure has been shown for the same, but the absorbent areas may also have the form of strips of greater or lesser widths, or of disc sectors (for example, if the mask is displaced in rotation). The ratio between the surface of the absorbent areas and that of the non-absorbent areas is not of critical nature. The method of the invention is sufficiently effective so that the distribution of the diffusion component may still be determined precisely whilst making use of a mask comprising up to 50% of absorbent areas. Beyond this proportion, the method loses its interest in the degree in which the diffusion component becomes so small during exposure of the fundamental images that it is no longer necessary to correct the same. The problem then comes down to reconstructing a utilisable image from several incomplete fundamental images, being a technique which in its principle comes to that of the so-called "travelling apertures" method. This amounts to stating that the invention covers all the technical equivalents of the means employed if these fall within the scope of the following claims.

What is claimed is:

1. A method for processing a radiological image of a structure, which image is obtained from an irradiation of the said structure by means of a beam of penetrating radiation emitted by a source, for example, an X-ray source, and comprising a significant component and an overll diffusion interference component, characterised in that it consists in:
    eliminating a finite number of parts of the said beam along different directions between the source and the said structure,
    detecting at least one fundamental radiological image under these conditions,
    deducing a distribution of the diffused radiation substantially throughout the image from the areas of the said fundamental image corresponding to the parts eliminated from the said beam,
    correcting the said fundamental image or possibly an analogous image by means of the said distribution of the diffused radiation.

2. A method according to claim 1, characterised in that it consists in selecting areas of the said fundamental image corresponding to the parts eliminated from the said beam, in making allowance for the diffused radiation intensities in these areas and in applying an interpolation method known per se so that from a knowledge of the intensity values of the said diffused radiation, it is possible to deduce other intensity values of the diffused radiation corresponding to other areas of the said image.

3. A method according to claim 1, characterised in that it consists in eliminating the said parts from the said beam by interposing a mask bearing a finite number of areas which are substantially wholly absorbent as regards the said radiation, between the said source and the said structure.

4. A method according to claim 3, characterised in that use is made of a mask of which the said absorbent areas form a regular geometric pattern, for example, with a periodicity along at least one direction of the plane of the mask.

5. A method according to claim 1, characterised in that a reference image is detected in the same conditions as the said fundamental image but in the absence of the said structure so as to secure precise determination of the said areas of the said fundamental image which correspond to the parts eliminated from the beam.

6. A method according to claim 2, characterised in that a reference image is detected in the same conditions as the said fundamental image but in the absence of the said structure so as to secure precise determination of the said areas of the said fundamental image which correspond to the parts eliminated from the beam and that the aforesaid selection of the areas of the said image corresponding to the parts eliminated from the said beam consists in performing a logic (AND) operation between the homologous elementary parts of the said fundamental image and of the said reference image.

7. A method according to claim 1, characterised in that it consists in correcting the said fundamental image or the said analogous image by subtracting from the same in image representing the said distribution of the diffused radiation.

8. A method according to claim 1, characterised in that the detection of the said fundamental image and/or of the said reference image is accompanied by a conversion into digital form of the one or both, and in that the subsequent operations preceding a visual display of the aforesaid corrected image are performed on the whole of the digital data thus obtained.

9. A method according to claim 1, characterised in that an aforesaid analogous image is produced from the said fundamental image by completing this latter with at least particular parts of another image of the said structure reproducing at least the said areas corresponding to the said parts eliminated from the said beam, this other image preferably being taken within a short time of the first.

10. A method according to claim 1, characterised in that a complementary image of the said structure is produced from a beam comprising only parts eliminated for producing the said fundamental image, and in that an addition is performed between the said corrected fundamental image and the said complementary image.

11. A method according to claim 10, characterised in that the said complementary image is produced by interposing a mask complementary to the said first mask, for and instead of the latter.

12. A method according to claim 1, characterised in that it consists in detecting two fundamental images from two beams not having any eliminated part in common, in correcting each of these fundamental images, in forming the mean of the homologous parts of the said corrected fundamental images which do not correspond to the parts eliminated from the one beam or the other and in adding the corrected parts of each fundamental image which correspond to the parts eliminated from the beam for producing the other fundamental image.

13. A method according to claim 1, characterised in that it consists in detecting two fundamental images from two beams not having any eliminated part in common, in establishing the average of the homologous parts of the said fundamental images which do not correspond to the parts eliminated from the one beam or the other, in adding thereto the parts of each fundamental image which correspond to the parts eliminated from the beam for producing the other fundamental image, in such manner as to obtain the said analogous image and as to correct this latter.

14. A method according to claim 12, characterised in that the two fundamental images are taken within a short time of each other by interposing a mask bearing a finite number of areas substantially wholly absorbed as regards the said radiation between the said source and the object and by displacing this mask between the two exposures of the fundamental images.

15. A method according to claim 14, characterised in that each of the two fundamental images is taken with a reduced radiation dosage.

16. A method according to claim 14, characterised in that the said mask is displaced within its own plane with an alternating linear displacement or a rotary displacement and in that the exposures of the two fundamental images are synchronised with this displacement.

17. A method according to claim 1, characterised in that an aforesaid analogous image is produced by a second exposure of the said structure taken within a short time of the exposure of the said fundamental image, this second exposure being taken from a complete irradiation beam and in that the resulting complete analogous image is corrected.

18. A method according to claim 1, characterised in that the missing parts of a possibly corrected fundamental image are completed by means of an interpolation known per se based on points close to the said missing parts, in the image itself.

* * * * *